United States Patent [19]

Chiou

[11] Patent Number: 5,266,580
[45] Date of Patent: Nov. 30, 1993

[54] TREATMENT OF LOW PRESSURE GLAUCOMA AND ISCHEMIC RETINAL DEGENERATION WITH DROPERIDOL

[75] Inventor: George C. Y. Chiou, College Station, Tex.

[73] Assignee: Texas A&M University System, College Station, Tex.

[21] Appl. No.: 825,661

[22] Filed: Jan. 24, 1992

[51] Int. Cl.$^5$ ............................................. A61K 31/44
[52] U.S. Cl. ................................... 514/338; 514/912
[58] Field of Search ............................... 514/338, 912

[56] References Cited

U.S. PATENT DOCUMENTS

| | | | |
|---|---|---|---|
| 4,501,749 | 2/1985 | Clineschmidt | 514/326 |
| 4,521,414 | 6/1985 | Chiou et al. | 514/229 |
| 4,565,821 | 6/1986 | Chiou | 514/327 |
| 4,772,616 | 9/1988 | Chiou | 514/322 |
| 4,886,795 | 12/1989 | Schachar | 514/211 |

OTHER PUBLICATIONS

Weinreb, R., *Eye Research Seminar*, Research to Prevent Blindness, (1990) pp. 14–16.
Chandler et al., *Lectures on Glaucoma*, Lea & Febiger, Philadelphia, (1965) pp. 111–115.
Lierman, *Building a Healthy America*, Mary Ann Liebert, Inc., New York, (1987) pp. 115–119.
U.S. Department of Health and Human Services, *Vision Research, Report of Retinal and Choroid Diseases Panel*, NIH Publication No. 83-2471 (1983).
LeVail et al., Eds., *Retinal Degeneration, Experimental and Clinical Studies*, Alan R. Liss, Inc., New York (1985).
Chiou et al., *Ophthalmic Res.* (1984) 16:129–134.
Chiou et al., *J. Ocular Pharmacology* (1989) 5(4):281–292.
Yan et al., *Ophthalmic Res.* (1987) 19:45–48.
Chiou et al., *Ophthalmic Res.* (1983) 15:131–135.
Chiou, *Arch. Ophthalmol.* (1984) 102:143–145.
Muller et al., *Life Science* (1981) 29:867–883.
Potter et al., *Gen. Pharmacol.* (1981) 12:1–13.
Ramos et al., *Rev. Fac. Farm. Bioquim. S. Paulo* (1966) 4(2):259–263.
Schmiedeberg et al., *Arch. Klin. Exp. Ophthal.* (1971) 183:179–195.
Shannon et al., *Invest. Ophthalmol.* (1976) 15(5):371–380.
Wantanabe et al., *Ophthalmic Res.* (1983) 15:160–167.
Farmakol. Toksikol. (USSR), 1984, 47/4 (59–62). Yakushev et al.

*Primary Examiner*—Zohreh A. Fay
*Attorney, Agent, or Firm*—Morrison & Foerster

[57] ABSTRACT

The invention relates to a method for increasing blood flow to the retina and choroid in subjects with decreased retinal or choroidal blood flow. The method involves the topical administration of droperidol and is useful for the treatment of low pressure glaucoma and ischemic retinal degeneration.

16 Claims, No Drawings

TREATMENT OF LOW PRESSURE GLAUCOMA AND ISCHEMIC RETINAL DEGENERATION WITH DROPERIDOL

TECHNICAL FIELD

The present invention relates generally to a method for the improvement of blood flow to the retina and choroid in order to halt or reverse the course of visual deterioration. More specifically, it relates to the treatment of ischemic retinal degeneration and low pressure glaucoma.

BACKGROUND OF THE INVENTION

Glaucoma is a leading cause of blindness affecting approximately 3 million people in the United States. About one-third of the patient population afflicted with glaucoma suffers from what is known as low tension glaucoma. R. Weinreb, *Eye Research Seminar*, Research to Prevent Blindness, (1990) p. 14–15. This type of glaucoma is not associated with elevated intraocular pressure (IOP). However, antiglaucoma agents are generally designed to lower the IOP in order to improve the ocular blood flow, particularly at the choroid, retina and lamina cribosa of the optic nerve. Such antiglaucoma agents are ineffective for the treatment of low tension glaucoma, as the IOP of these patients is already low. Therefore most low tension glaucoma patients undergo a filtering operation instead of being treated with antiglaucoma drugs. Chandler et al. Glaucoma, Lea & Febiger, Philadelphia, 111-115 (1965).

Ischemic retinal degeneration, or degeneration of the central part of the retina, is the second leading cause of blindness among people of all ages. It causes at least some loss of vision in 10 million people over the age of 50. Lierman, *Building a Healthy America*, Mary Ann Liebert Inc., New York 115-119 (1987). This ischemic retinal degeneration is caused by various diseases, including diabetic retinopathy, glaucoma, sickle cell retinopathy, vascular abnormalities, obstructive arterial and venous retinopathies, venous capillary insufficiency, hypertensive retinopathy, inflammation, tumors, retinal detachment, etc. U.S. Dept of Health & Human Services, *Vision Research, Report of Retinal and Choroid Diseases Panel*, NIH Publication #83-2471 (1983). LeVail et al., *Retinal Degeneration, Experimental and Clinical Studies*, Alan R. Liss Inc., New York (1985).

The retina is supplied with oxygen and nutrients by two vascular systems, one within the retina itself (central retinal artery) and one in the choroid (posterior ciliary artery). Interruption or impairment of either system leads to degeneration of the retina and ultimately to loss of vision. There are many diseases and conditions that affect retinal circulation and nutritional supply. Early improvement in blood flow or nutrient supply to the retina in some of these diseases and throughout the time course of others might be the key to slowing vision loss or eliminating it altogether.

Various dopamine antagonists have been shown to lower IOP. U.S. Pat. Nos. 4,565,821 and 4,772,616 describe the use of butypherones (i.e. haloperidol, trifluperidol and moperone) and domperidone to lower intraocular pressure. U.S. Pat. No. 4,521,414 describes the use of the R isomer of timolol as an anti-hypertensive agent for the eye. The use of the dopamine antagonists haloperidol, moperone, trifluperidol, clofluperol, pipamperone and lemperone in the treatment of ocular hypertension and glaucoma is also described. Chiou, *Ophthal. Res.* 16:129-134 (1984).

Although the foregoing references describe the use of dopamine antagonists to decrease IOP, Chiou et al., *J. Ocular Pharmacy*, 5:281-292 (1989) found that some dopamine antagonists increase IOP as well. Chiou et al. hypothesized that dopamine antagonists may decrease ciliary blood flow at post-synaptic sites in order to lower the IOP and improve ocular blood flow.

It has also been shown that all dopamine antagonists do not act on ocular blood flow uniformly. For example, haloperidol, moperone and trifluperidol were found to reduce the blood flow to the retina and choroid. Chiou et al., *Ophthal. Res.* 18:265-269 (1986), and Yan et al. *Ophthal. Res.* 19:45-48 (1987). Although domperidone was found to increase the retinal blood flow, it also caused eye irritation.

DISCLOSURE OF THE INVENTION

The present invention is based on the finding that certain dopamine antagonists increase ocular blood flow without eye irritation. Thus, these drugs provide a convenient means for treating or preventing visual deterioration associated with decreased blood flow.

Accordingly, the present invention relates to a method to increase blood flow to the retina or choroid in a subject with decreased retinal and choroidal blood flow. The method involves administering a therapeutically effective amount of droperidol to the subject.

In one aspect, the invention is drawn to the use of droperidol to increase blood flow to the retina for the treatment of low pressure glaucoma.

In a second aspect, the invention is drawn to the use of droperidol to increase blood flow to the retina for the prevention of ischemic retinal degeneration.

In another embodiment, the invention relates to a method to prevent or treat visual deterioration associated with decreased choroidal or retinal blood flow. The method comprises administering a therapeutically effective amount of droperidol to a subject with decreased blood flow.

In a further embodiment, the invention relates to an ocular delivery device comprising droperidol.

In yet another embodiment, the invention relates to a pharmaceutical composition comprising droperidol in admixture with a pharmaceutically acceptable vehicle. The composition is useful for the treatment or prevention of visual deterioration associated with diseases or conditions that reduce blood flow to the retina and choroid.

DETAILED DESCRIPTION OF THE INVENTION

The present invention is applicable to the treatment or prevention of visual deterioration associated with diseases or conditions that decrease retinal or choroidal blood flow. Droperidol has been shown to increase the blood flow at the retina and choroid. Low tension glaucoma and ischemic retinal degeneration appear to be associated with decreased ocular blood flow. Accordingly, the use of droperidol affords a method for treating these disorders. Additionally, droperidol does not produce local irritation to the eyes.

Droperidol is a commercially available substance with the following structure:

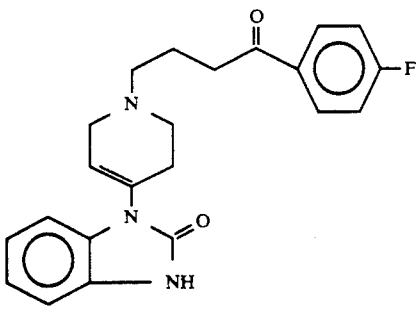

Definitions

In this specification and in the claims which follow, reference will be made to a number of terms which shall be defined to have the following meanings:

"Decreased blood flow" as used herein refers to choroidal or retinal blood flow that is below normal human retinal blood flow. Normal blood flow has been reported in the range of 8.1 to 18.5 $\mu$l/min/mg tissue.

"Treatment" as used herein refers to the reduction or elimination of visual deterioration resulting from decreased blood flow to the retina and choroid (therapy).

"Prevention" refers to the treatment of patients with decreased retinal and/or choroidal blood flow to avoid visual deterioration (prophylaxis).

"Pharmaceutically active substance" as used herein refers to a substance that has been shown to be useful in the treatment of decreased ocular blood flow. In the present invention, pharmaceutically active substances include droperidol.

"Pharmaceutical composition" refers to a composition containing the pharmaceutically active substance. The composition may also contain a pharmaceutically acceptable vehicle.

"Therapeutically effective amount" as used herein refers to an amount of a pharmaceutically active substance useful in the prevention or treatment of visual deterioration.

"Ischemic retinal degeneration" is the degeneration of the retina and occurs as a result of the impairment or interruption of the supply of oxygen or other nutrients to the retina via the central retinal artery or to the choroid via the posterior ciliary artery. Such impairment or interruption may result from various diseases and conditions such as diabetic retinopathy, glaucoma, sickle cell retinopathy, vascular abnormalities, obstructive arterial and venous retinopathies, venous capillary insufficiency, hypertensive retinopathy, inflammation, tumors, and retinal detachment.

ADMINISTRATION

The administration of droperidol can be via any of the accepted modes of administration of pharmaceutical compositions. These methods include topical administration of solutions, suspension ointments or gels, parenteral injection, or oral administration.

Depending on the intended mode of administration, the compositions may be in the form of solid, semi-solid or liquid dosage forms, such as for example, tablets, pills, capsules, powders, liquids, suspensions, or the like, preferably in unit dosage forms suitable for single administration of precise dosages. The compositions will include a conventional pharmaceutical vehicle and, in addition, may include other medicinal agents, pharmaceutical agents, carriers, adjuvants, diluents, etc. The amount of active compound administered will, of course, be dependent on the subject being treated, the manner of administration and the judgment of the prescribing physician.

The conventional pharmaceutical vehicle should be compatible with the pharmaceutically active substance of the pharmaceutical composition. Suitable vehicles for ocular use are, for example, sterile isotonic solutions such as isotonic sodium chloride or boric acid solutions. These vehicles typically contain sodium chloride or boric acid, respectively, as well as benzalkonium chloride and sterile distilled or purified water. Also useful is phosphate buffered saline (PBS), pH 7.4. Other suitable vehicular constituents include phenylmercuric nitrate, sodium sulfate, sodium sulfite, disodium phosphate and monosodium phosphate.

The compositions may also contain auxiliary substances, i.e. antimicrobial agents such as chlorobutanol, parabens or organic mercurial compounds; pH adjusting agents such as sodium hydroxide, hydrochloric acid or sulfuric acid; and viscosity increasing agents such as methylcellulose. One of ordinary skill in the art will easily find substitutes for the above auxiliary substances. The final composition should be sterile, essentially free of foreign particles, and have a pH that allows for optimum drug stability. Generally, pH values in the range of 5–8 will find use with the subject composition. Preferably, the pH will be as close to the pH of tear fluid, i.e. 7.4 as possible.

Typically, the compositions of the subject invention are prepared as solutions, suspensions, ointments, gels, or ocular delivery devices such as drug-impregnated solid carriers that are inserted into the eye. If such a carrier is used, the above-mentioned vehicles are unnecessary. A variety of polymers can be used to formulate ophthalmic drug carriers. Saettone, M. F., et al., *J. Pharm. Pharmocol* (1984) 36:229, and Park, K. et al., in *Recent Advances in Drug Delivery Systems*, Anderson et al., eds., Plenum Press (1984) 163–183, describe such polymers, the disclosures of which are incorporated herein by reference in their entirety. Drug release is generally effected via dissolution or bioerosion of the polymer, osmosis, or combinations thereof. The device should be formulated to release the drug at a rate that does not significantly disrupt the tonicity of tear fluid.

More specifically, several matrix-type delivery systems can be used with the subject invention. These systems are described in detail in Ueno et al., "Ocular Pharmacology of Drug Release Devices", in *Controlled Drug Delivery*, Bruck, ed., vol. II, Chap 4 CRC Press Inc. (1983), the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate, and vinylpyrrolidone, as well as cross-linked polypeptides or polysaccharides, such as chitin.

Capsule-type delivery systems will also find use with the instant invention. These systems, described in Ueno et al., supra, utilize polymer membranes to control the release of the drug in question. These devices are particularly useful for the delivery of hydrophilic drugs. Hydrophobic drugs can be administered via a silicone rubber device such as described in Ueno et al., supra.

Ophthalmic ointments will include a base, generally composed of white petrolatum and mineral oil, often with anhydrous lanolin. Polyethylene-mineral oil gel is also satisfactory, as are other substances that are non-irritating to the eye, permit diffusion of the drug into the ocular fluid, and retain activity of the medicament for a reasonable period of time under storage conditions. If suspensions are used, the particle sizes therein should be less than 10 μm to minimize eye irritation. Furthermore, if solutions or suspensions are used, the amount delivered to the patient should not exceed 50 μl, preferably 25 μl or less, to avoid excessive spillage from the eye.

For solid compositions, conventional nontoxic solids including, for example, pharmaceutical grades of mannitol, lactose, starch, magnesium stearate, sodium saccharin, talc, cellulose, glucose, sucrose, magnesium carbonate, and the like may be used. Liquid pharmaceutically administrable compositions can, for example, be prepared by dissolving, dispersing, etc. an active compound as defined above and optional pharmaceutical adjuvants in a vehicle, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art, for example, see *Remington's Pharmaceutical Sciences*, Mack Publishing Company, Easton, Pa., 15th Edition, 1975.

For topical administration, i.e. application of solutions, suspensions, ointments, gels, etc. directly to the eye, the composition may contain 0.01-10.0% active ingredient, preferably 0.1-1.0%. An effective amount for the purposes of preventing or treating visual deterioration is usually in the range of 0.01-0.1 mg/kg. The compound may be administered every 4-8 hours. Preferably, the compound is administered every 6 hours.

The subject compounds can also be administered by implantation of a slow-release or sustained-release system, such that a constant level of dosage is maintained. For a review of these sustained release systems see Ueno, et al., "Ocular Pharmacology of Drug Release Devices", in *Controlled Drug Delivery*, Bruck, ed., vol. II, Chap 4, CRC Press Inc. (1983). The pharmaceutically effective amount of droperidol to halt or reverse the course of visual deterioration is usually in the range of 0.1-2.0 mg/day. A new implant should be inserted every 3-10 days. Preferably, a new implant is inserted every 5-7 days.

For oral administration, a pharmaceutically acceptable nontoxic composition is formed by the incorporation of any of the normally employed vehicles described above. Such compositions take the form of solutions, suspensions, tablets, pills, capsules, powders, sustained-release formulations and the like. Such compositions may contain 1-95% active ingredient, preferably 1-10%. An effective amount for the purposes of preventing or treating visual deterioration is usually in the range of 0.01-0.1 mg/kg. The compound may be administered every 4-8 hours. Preferably, the compound is administered every 6 hours.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable vehicles are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as, for example, sodium acetate, sorbitan monolaurate, triethanolamine oleate, etc. An effective amount for the purposes of preventing or treating visual deterioration is usually in the range of 0.01-0.1 mg/kg. The compound is administered as described above with regard to oral administration.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1

Preparation of an Animal Model for Ocular Blood Flow

A. Materials

L-Timolol was obtained from Merck, Sharp and Dohme (West Point, Pa.). Droperidol was purchased commercially from Janssen Pharmaceuticals Inc. (Piscataway, N.J.). Colored microspheres were purchased from E-Z Trac (Los Angeles, Calif.). The colored microspheres were diluted with saline containing 0.01% v/v of Tween 80 to keep the microspheres from sticking together. One million microspheres were injected at each time point.

B. Methods

New Zealand albino rabbits, weight 2.5-3.0 kg, were anesthetized with 35 mg/kg ketamine and 5 mg/kg xylazine intramuscularly. Half of the initial dose was given at one hour intervals afterward to maintain adequate anesthesia. The left ventricle of the heart was cannulated through the right carotid artery for microsphere injection, and the femoral artery was cannulated for blood sampling. The blood flow was measured with colored microspheres at −30 min for normal ocular blood flow and at 0 min for ocular blood flow with an IOP of 40 mm Hg. Droperidol eyedrops were instilled topically at time 0 min, and the blood flow was determined at 30, 60, 120, and 180 minutes thereafter. At each injection of microspheres, blood samples were taken from the femoral artery for exactly 60 seconds immediately after the injection of the microspheres as a reference.

After the last injection of the microspheres and the collection of blood samples, the animals were euthanized. The eyes were enucleated and dissected into the retina, choroid, iris and ciliary body. The tissue samples were weighed. The blood sample was collected in a heparinized tube, and the volume was recorded.

The details of sample processing and microsphere counting were provided by E-Z Trac. Tissue samples were added to Tissue/Blood Digest Reagent I in the microfuge tubes, sealed and heated at 95° C. for 15 minutes. They were vigorously vortexed for 15-30 seconds, then reheated and revortexed until the tissue samples were all dissolved. Tissue/Blood Digest Reagent II was then added while the samples were hot, and the tubes were capped and vortexed. The tubes were then centrifuged to settle the microspheres to the bottom of the tubes. The supernatant was aspirated, and the pellet was resuspended in the precise volume of Microsphere Counting reagent with vortex. If the sediment aggregated, it was dispersed with an ultrasonic bath. The number of various colored microspheres were then counted with a hemocytometer.

Hemolysis Reagent was added to the blood sample, vortexed, and centrifuged in a low speed centrifuge for 30 minutes. The supernatant was aspirated, and the Tissue/Blood Digest Reagent I was added. The procedure was the same as described above to process tissue samples, and the colored microspheres were counted with a hemocytometer.

C. Results

The blood flow of each tissue at a certain time point was calculated from the following equation:

$$Q_m = (C_m \times Q_r)/C_r$$

where $Q_m$ is the blood flow of a tissue in terms of $\mu l/min/mg$. $C_m$ is the microsphere count per mg of tissue, $Q_r$ is the flow rate of blood sample in terms of $\mu l/min$, and $C_r$ is the microsphere count in the referenced blood sample.

All data were expressed as mean ± standard error of the mean. Student's t-test was used to analyze the significance between the two means. The blood flow was considered significantly different from the control values at $p < 0.05$.

The ocular blood flow of normotensive animals is presented in Table 1. When the IOP was raised to 40 mm Hg, the blood flow was reduced to approximately ⅓ of the normal blood flow. The reduced blood flow remained stable during the entire experimental period of 3 hours. This is an animal model with reduced ocular blood flow and is useful for testing the effects of drugs to improve the ocular blood flow.

Example 2

The Effects of Droperidol on Ocular Blood Flow

50 μl of 0.25% droperidol eyedrops were instilled into the eyes of the animal models described in Example 1. There was a tendency for the blood flow to increase in all ocular tissues (iris, ciliary body, retina and choroid) at 30 min., although it was not statistically significant (Table 2). At 60, 120, and 180 minutes after drug instillation, the blood flow in all eye tissues increased significantly as compared to the control values at time 0 min. At 180 min after drug instillation, the blood flow in all ocular tissues was still increasing, indicating that the duration of action lasts longer than three hours (Table 2).

Example 3

The Effects of L-Timolol on Ocular Blood Flow

25 μl of 0.5% timolol was installed into the eyes of the animal models prepared in Example 1. The blood flow in the choroid was reduced significantly after drug instillation. the blood flow recovered to control levels at 60 min and then all increased significantly at 120 and 180 min (Table 3). These results indicate that timolol produced biphasic actions on the ocular blood flow by reducing it initially and then increasing it.

Example 4

Eye Irritation

50 μl of 0.25% droperidol was used to test for eye irritation in New Zealand white rabbit eyes using the standard procedure of the Draize Test. J. Draize et al., *J. Pharmacol. Exp. Ther.*, 82:377-390 (1944). Eyedrops were instilled in the eyes, and the responses of the eyes were examined with a slit lamp biomicroscope. Eye irritation was either absent or insignificant.

Modifications of the above described modes for carrying out the invention that are obvious to persons of skill in the art to which the invention pertains are intended to be within the scope of the invention.

TABLE 1

Effect of Ocular Hypertension at IOP of 40 mmHg on Ocular Blood Flow

| | Normotensive Eyes (N = 5) | Blood Flow (μl/min/mg tissue) Time After Exertion of IOP at 40 mmHg | | | | |
|---|---|---|---|---|---|---|
| Tissues | | 0 min (N = 9) | 30 min (N = 5) | 60 min (N = 5) | 120 min (N = 5) | 180 min (N = 4) |
| Iris | 1.83 ± 0.33[a] | 0.86 ± 0.25 | 0.83 ± 0.24 | 0.76 ± 0.23 | 0.74 ± 0.26 | 0.60 ± 0.05 |
| Ciliary Body | 1.88 ± 0.26 | 0.69 ± 0.26 | 0.58 ± 0.20 | 0.65 ± 0.19 | 0.66 ± 0.19 | 0.63 ± 0.08 |
| Retina | 0.21 ± 0.023 | 0.068 ± 0.009 | 0.057 ± 0.007 | 0.065 ± 0.005 | 0.057 ± 0.006 | 0.059 ± 0.005 |
| Choroid | 13.25 ± 0.81 | 4.30 ± 0.84 | 3.87 ± 0.73 | 3.65 ± 0.78 | 3.52 ± 0.76 | 3.05 ± 0.27 |

[a]Mean ± SEM

TABLE 2

Effect of 50 μl of 0.25% Droperidol on Ocular Blood Flow of Rabbit Eyes

| | Normotensive Eyes | Blood Flow (μl/min/mg tissue) Time After Drug Instillation with IOP of 40 mmHg | | | | |
|---|---|---|---|---|---|---|
| Tissues | | 0 min (control) | 30 min | 60 min | 120 min | 180 min |
| Iris | 1.57 ± 0.14[a] | 0.46 ± 0.084 | 0.62 ± 0.10 | 1.28 ± 0.22[b] | 1.33 ± 0.23[b] | 1.43 ± 0.30[b] |
| Ciliary Body | 2.04 ± 0.16 | 0.56 ± 0.13 | 0.86 ± 0.17 | 1.52 ± 0.23[b] | 1.58 ± 0.21[b] | 1.54 ± 0.37[b] |
| Retina | 0.25 ± 0.016 | 0.062 ± 0.006 | 0.079 ± 0.012 | 0.14 ± 0.024[b] | 0.16 ± 0.021[b] | 0.16 ± 0.02[b] |
| Choroid | 12.46 ± 0.63 | 3.34 ± 0.46 | 4.29 ± 0.68 | 6.14 ± 0.68[b] | 8.19 ± 1.02[b] | 8.65 ± 1.27[b] |

[a]Mean ± SEM of N = 4 for all except N = 8 for control.
[b]Statistically different from controls at time 0 min.

TABLE 3

Effects of 25 μl of 0.5% Timolol on Ocular Blood Flow of Rabbit Eyes

| Tissues | Normotensive Eyes (N = 5) | Blood Flow (μl/min/mg tissues) Time after Drug Instillation with IOP of 40 mmHg | | | | |
|---|---|---|---|---|---|---|
| | | 0 min (control) (N = 9) | 30 min (N = 5) | 60 min (N = 5) | 120 min (N = 5) | 180 min (N = 4) |
| Iris | 1.33 ± 0.14[a] | 0.32 ± 0.038 | 0.25 ± 0.036 | 0.60 ± 0.10 | 1.06 ± 0.15[b] | 1.96 ± 0.32[b] |
| Ciliary Body | 1.71 ± 0.23 | 0.35 ± 0.057 | 0.31 ± 0.072 | 0.82 ± 0.21 | 1.40 ± 0.18[b] | 2.19 ± 0.26[b] |
| Retina | 0.22 ± 0.017 | 0.058 ± 0.006 | 0.055 ± 0.006 | 0.079 ± 0.011 | 0.20 ± 0.015[b] | 0.18 ± 0.017[b] |
| Choroid | 13.15 ± 1.10 | 3.50 ± 0.55 | 1.61 ± 0.20[b] | 3.73 ± 1.15 | 7.79 ± 1.82[b] | 10.18 ± 0.82[b] |

[a] Mean ± SEM
[b] Statistically different form controls at time 0 min.

I claim:

1. A method to increase blood flow to the retina or choroid which method comprises administering a therapeutically effective amount of droperidol to a subject having decreased retinal or choroidal blood flow.

2. The method of claim 1 wherein the decreased retinal or choroidal blood flow is due to low pressure glaucoma.

3. The method of claim 1 wherein the decreased retinal or choroidal blood flow is due to ischemic retinal degeneration.

4. The method of claim 3 wherein the ischemic retinal degeneration is caused by a disease selected from the group consisting of diabetic retinopathy, glaucoma, sickle cell retinopathy, vascular abnormalities, obstructive arterial and venous retinopathies, venous capillary insufficiency, hypertensive retinopathy, inflammation, tumors, and retinal detachment.

5. The method of claim 1 wherein the droperidol is administered topically.

6. The method of claim 1 wherein the droperidol is administered parenterally.

7. The method of claim 1 wherein the droperidol is administered orally.

8. The method of claim 5 wherein topical administration is accomplished through the use of an ocular delivery device.

9. A method for the treatment of visual deterioration associated with decreased retinal or choroidal blood flow which method comprises administering a therapeutically effective amount of droperidol to a subject having said decreased retinal or choroidal blood flow.

10. The method of claim 9 wherein the decreased retinal or choroidal blood flow is due to low pressure glaucoma.

11. The method of claim 9 wherein the decreased retinal or choroidal blood flow is due to ischemic retinal degeneration.

12. The method of claim 11 wherein the ischemic retinal degeneration is caused by a disease selected from the group consisting of diabetic retinopathy, glaucoma, sickle cell retinopathy, vascular abnormalities, obstructive arterial and venous retinopathies, venous capillary insufficiency, hypertensive retinopathy, inflammation, tumors, and retinal detachment.

13. The method of claim 9 wherein the droperidol is administered topically.

14. The method of claim 9 wherein the droperidol is administered parenterally.

15. The method of claim 9 wherein the droperidol is administered orally.

16. The method of claim 13 wherein topical administration is accomplished through the use of an ocular delivery device.

* * * * *